United States Patent [19]
Croce et al.

[11] 3,937,746

[45] Feb. 10, 1976

[54] SULFUR PROMOTED OXIDATIVE DEHYDROGENATION

[75] Inventors: Louis J. Croce, Seabrook, Tex.; Laimonis Bajars, Princeton, N.J.

[73] Assignee: Petro-Tex Chemical Corporation, Houston, Tex.

[22] Filed: June 23, 1971

[21] Appl. No.: 156,086

Related U.S. Application Data

[62] Division of Ser. No. 859,565, Sept. 19, 1969, Pat. No. 3,666,687.

[52] U.S. Cl. .......................... 260/669 R; 260/680 E
[51] Int. Cl.² ............................................ C07C 5/20
[58] Field of Search ..................... 260/680 E, 669 R

[56] References Cited
UNITED STATES PATENTS

| | | | |
|---|---|---|---|
| 3,284,536 | 11/1966 | Bajars et al. | 260/680 X |
| 3,373,213 | 3/1968 | Pasternak et al. | 260/666 |
| 3,403,192 | 9/1968 | Vadekar et al. | 260/666 |
| 3,450,788 | 6/1969 | Kehl et al. | 260/680 |
| 3,567,793 | 3/1971 | Colling et al. | 260/680 |
| 3,585,249 | 6/1971 | Cohen et al. | 260/669 |
| 3,590,090 | 6/1971 | Cohen et al. | 260/669 |

*Primary Examiner*—C. Davis
*Attorney, Agent, or Firm*—N. Elton Dry; Kenneth H. Johnson

[57] ABSTRACT

The yield in oxidative dehydrogenation of organic compounds is improved by having a surfur promoter present either as part of the catalyst or added to the reaction with the reactants.

52 Claims, No Drawings

SULFUR PROMOTED OXIDATIVE DEHYDROGENATION

This application is a division of Ser. No. 859,565, filed Sept. 19, 1969 now U.S. Pat. No. 3,666,687.

The present invention relates to the oxidative dehydrogenation of organic compounds over ferrite catalysts wherein the oxidative dehydrogenation system is modified by the presence of sulfur.

Oxidative dehydrogenations employing ferrite catalysts are well known. U.S. Pat. Nos. 3,270,080; 3,284,536; 3,303,234; 3,303,235; 3,303,236; 3,303,238; 3,308,182; 3,324,195; 3,334,152; 3,342,890; 3,398,100 and 3,450,787 disclose such processes.

Briefly stated the present invention is a process for the oxidative dehydrogenation of organic compounds in the presence of an oxygen containing gas, a metal ferrite catalyst and sulfur. Although excellent results have been obtained with many of the catalysts described in the prior art, it is an object of this invention to provide further improved catalysts. It is a principal object of this invention to increase the conversion, selectivity and yield obtained with the catalyst. Another object is to improve the strength of the catalyst. These and other objects will become obvious from the following description of the invention.

As stated above the presence of sulfur in the oxidative dehydrogenation in the essential feature of the present invention. The presence of sulfur in the oxidative dehydrogenation can be achieved by incorporating the sulfur into the metal ferrite catalyst or the sulfur can be added to the reaction along with the reactants. The mechanism involved for the two types of sulfur addition may or may not be the same; however, no mechanism is proposed. In any event the results are essentially the same regardless of the manner of incorporating sulfur in the reaction system.

The sulfur can be incorporated into metal ferrite catalysts in the form of an iron sulfate, sulfite or sulfide such as iron (II) sulfate, iron (III) sulfate, iron (II) sulfite, iron (II) sulfide, iron (III) sulfide and the hydrates thereof. Similarly, the sulfur can be incorporated in the catalyst in the form of a sulfide, sulfite or sulfate of a metal other than iron. For example, magnesium sulfate, barium sulfate, lanthanum sulfate, cobaltic sulfate, cobaltous sulfate, manganese (II) sulfate, nickel sulfate, zinc sulfate, magnesium sulfide, magnesium sulfite, nickel sulfide, nickel sulfite, manganese (III) sulfate, manganese (IV) sulfide, zinc sulfide, zinc sulfite, calcium sulfite, calcium sulfate, cadmium sulfate and the like. Sulfur can also be incorporated into metal ferrite catalyst by way of sulfuric acid, oleium, sulfurous acid and so forth. The sulfur should be present in an amount sufficient to promote the catalyst, generally of from about 0.001 to 0.50 atoms of sulfur per atom of iron in the catalyst and presumably between about 0.005 and 0.10 atom of sulfur per atom of iron.

The second mode of sulfur addition to the oxidative dehydrogenation is along with the reactants, i.e. during the reaction. This is conveniently done by the use of oxides of sulfur, typically sulfur dioxide and sulfur trioxide. Other compounds particularly those that are vaporous under the reaction conditions can be used; for example, such as sulfuryl chloride, sulfuryl fluoride, sulfuryl chloride fluoride, sulfur oxytetrachloride, sulfur bromide, sulfur chloride, sulfur trichloride, hydrogen sulfide, and the like. Sulfuric acid is also conveniently added to the reaction. The sulfur compound can be added with the organic reactant feed to the reaction or the oxygen containing gas. The sulfur is added to the reaction zone in an amount sufficient to promote the reaction, generally in a ratio of gram atoms of sulfur to a mole of the organic reactant of between about 0.0003:1.0 to 0.50:1.0 and more preferably 0.001:1.0 to 0.05:1.0.

It has been found that a preferred class of sulfur promoter compounds described above for addition to the catalyst or to the reaction contain oxygen, for example, the sulfites or sulfates, or the oxides of sulfur. The sulfur compound can be added continuously or incrementally to the feed.

In addition to the types of sulfur compounds described above any other sulfur containing compound is effective to achieve the improvements of this invention including the thiocyanates, thiosulfates, persulfates and organic sulfur containing compounds, e.g. methyl mercaptan, ethyl mercaptan, etc.

Although the invention is described in terms of adding the sulfur to the catalyst or to the reaction, sulfur can be added to both. Specified herein above are certain ranges of sulfur content in relation to the catalyst or organic feed to the oxidative dehydrogenation, however, larger quantities of sulfur can be present in the reaction. The upper limit of sulfur content recited is based on economic considerations and the increasing by-product production at substantially higher sulfur concentrations. The lower limit of acceptable sulfur concentration is that which will produce an improvement in the reaction. The recited lower limits of sulfur concentration are intended to point out a reasonable lower limit, although some improvement may be detectable at still lower concentrations.

The addition of sulfur compounds can not only improve the catalytic properties of the compounds but will also make a sturdier and stabler catalyst.

The process of this invention may be applied to the dehydrogenation of a wide variety of organic compounds. Such compounds normally will contain from 2 to 20 carbon atoms, at least one

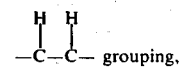
—C—C— grouping, a boiling point below about 350°C., and such compounds may contain other elements, in addition to carbon and hydrogen such as oxygen, halogens, nitrogen and sulfur. Preferred are compounds having 2 to 12 carbon atoms, and especially preferred are compounds of 3 to 6 or 8 carbon atoms.

Among the types of organic compounds which may be dehydrogenated by means of the process of this invention are nitriles, amines, alkyl halides, ethers, esters, aldehydes, ketones, alcohols, acids, alkyl aromatic compounds, alkyl heterocyclic compounds, cycloalkanes, alkanes, alkenes, and the like. Illustration of dehydrogenations include propionitrile to acrylonitrile; propionaldehyde to acrolein; ethyl chloride to vinyl chloride; methyl isobutyrate to methyl methacrylate; 2 or 3 chlorobutene-1 or 2,3,dichlorobutane to chloroprene; ethyl pyridine to vinyl pyridine; ethylbenzene to styrene; isopropylbenzene to α-methyl styrene; ethylcyclohexane to styrene; cyclohexane to benzene;

ethane to ethylene or acetylene; propane to propylene, methyl acetylene, allene, or benzene; isobutane to isobutylene; n-butane and butadiene-1,3; n-butene to butadiene-1,3 and vinyl acetylene; methyl butene to isoprene; cyclopentane to cyclopentene and cyclopentadiene-1,3; n-octane to ethyl benzene and ortho-xylene; monomethylheptanes to xylenes; ethyl acetate to vinyl acetate; 2,4,4-trimethylpentane to xylenes; and the like. This invention may be useful for the formation of new carbon to carbon bonds by the removal of hydrogen atoms such as the formation of a carbocyclic compound from two alkphatic hydrocarbon compounds or the formation of a dicyclic compound from a monocyclic compound having an acyclic group such as the conversion of propene to diallyl. Representative materials which are dehydrogenated by the novel process of this invention include ethyl toluene, alkyl chlorobenzenes, ethyl naphthalene, isobutyronitrile, propyl chloride, isobutyl chloride, ethyl fluoride, ethyl bromide, n-pentyl iodide, ethyl dichloride, 1,3-dichlorobutane, 1,4-dichlorobutane, the chlorofluoroethanes, methyl pentane, methylethyl ketone, diethyl ketone, n-butyl alcohol, methyl propionate, and the like.

Suitable dehydrogenation reactions are the following: acylic compounds having 4 to 5 non-quarternary contiguous carbon atoms to the corresponding olefins, diolefins or acetylenes having the same number of carbon atoms; aliphatic hydrocarbons having 6 to 16 carbon atoms and at least one quarternary carbon atom to aromatic compounds, such as 2,4,4-trimethylpentene-1 to a mixture of xylenes; acyclic compounds having 6 to 16 carbon atoms and no quarternary carbon atoms to aromatic compounds such as n-hexenes to benzene; cycloparaffins and cycloolefins having 5 to 8 carbon atoms to the corresponding olefin, diolefin or aromatic compound, e.g., cyclohexane to cyclohexene or cyclohexadiene or benzene; aromatic compounds having 8 to 12 carbon atoms including one or two alkyl side chains of 2 ro 3 carbon atoms to the corresponding aromatic with unsaturated side chain such as ethyl benzene to styrene.

The preferred compounds to be dehydrogenated are hydrocarbons with a particularly preferred class being acyclic non-quarternary hydrocarbons having 4 to 5 contiguous carbon atoms or ethyl benzene and the preferred products are n-butene-1 or 2, butadiene-1, 3, vinyl acetylene, 2-methyl-1-butene, 3-methyl-1-butene, 3-methyl-2-butene, isoprene, styrene or mixtures thereof. Especially preferred as feed are n-butene-1 or 2 and the methyl butenes and mixtures thereof such as hydrocarbon mixtures containing these compounds in at least 50 mol percent.

The dehydrogenation reaction may be carried out at atmospheric pressure, superatmospheric pressure or at sub-atmospheric pressure. The total pressure of the system will normally be about or in excess of atmospheric pressure, although sub-atmospheric pressure may also desirably be used. Generally, the total pressure will be between about 4 p.s.i.a. and about 100 or 125 p.s.i.a. Preferably, the total pressure will be less than about 75 p.s.i.a. and excellent results are obtained at about atmospheric pressure.

The organic compound to be dehydrogenated is contacted with oxygen in order for the oxygen to oxidatively dehydrogenate the compound. Oxygen may be fed to the reactor as pure oxygen, as air, as oxygen-enriched air, oxygen mixed with diluents, and so forth. Oxygen may also be added in increments to the dehydrogenation zone. Although determinations regarding the mechanism of reaction are difficult, the process of this invention is an oxidative dehydrogenation process wherein the predominant mechanism of this invention is by the reaction of oxygen with the hydrogen released from the hydrocarbon.

The amount of oxygen employed may vary depending upon the desired result such as conversion, selectivity and the number of hydrogen atoms being removed. Thus, to dehydrogenate butane to butene requires less oxygen than if the reaction proceeds to produce butadiene. Normally oxygen will be supplied (including all sources, e.g. air to the reactor) in the dehydrogenation zone in an amount from about 0.2 to 1.5, preferably 0.3 to 1.2, mols per mol of $H_2$ being liberated from the organic compound. Ordinarily the mols of oxygen supplied will be in the range of from 0.2 to 2.0 mols per mol of organic compound to be dehydrogenated and for most dehydrogenations this will be within the range of 0.25 to 1.5 mols of oxygen per mol of organic compound.

Preferably, the reaction mixture contains a quantity of steam or diluent such as nitrogen with the range generally being between about 2 and 40 mols of steam per mol of organic compound to be dehydrogenated. Preferably, steam will be present in an amount from about 3 to 35 mols per mol of organic compound to be dehydrogenated and excellent results have been obtained within the range of about 5 to about 30 mols of steam per mol of organic compound to be dehydrogenated. The functions of the steam are several-fold, and the steam may not merely act as a diluent. Diluents generally may be used in the same quantities as specified for the steam. These gases serve also to reduce the partial pressure of the organic compound.

It is one of the advantages of this invention that halogen may also be present in the reaction gases to give excellent results. The presence of halogen in the dehydrogenation zone is particularly effective when the compound to be dehydrogenated is saturated, such as a saturated hydrocarbon. The halogen present in the dehydrogenation zone may be either elemental halogen or any compound of halogen which would liberate halogen under the conditions of reaction. Suitable sources of halogen are such as hydrogen iodide, hydrogen bromide and hydrogen chloride; aliphatic halides, such as ethyl iodide, methyl bromide, methyl chloride, 1,2-dibromo ethane, cycloaliphatic halides, ammonium iodide; ammonium bromide; ammonium chloride; sulfuryl chloride; metal halides incuding molten halides; and the like. The halogen may be liberated partially or entirely by a solid source as disclosed in the process of U.S. Pat. No. 3,130,241 issued Apr. 21, 1964. Mixtures of various sources of halogen may be used. The amount of halogen, calculated as elemental halogen, may be as little as about 0.0001 or less mol of halogen per mol of the organic compound to be dehydrogenated to as high as 0.2 or 0.5.

The temperature for the dehydrogenation reaction generally will be at least about 250°C., such as greater than about 300° or 375°C., and the maximum temperature in the reactor may be about 700° or 800°C. or perhaps higher such as 900°C. under certain circumstances. However, excellent results are obtained within the range of or about 350° to 700°C., such as from or about 400° to or about 675°C. The temperatures are measured at the maximum temperature in the dehydrogenation zone.

The gaseous reactants may be conducted through the reaction chamber at a fairly wide range of flow rates. The optimum flow rate will be dependent upon such variables as the temperature of reaction, pressure, particle size, and so forth. Desirable flow rates may be established by one skilled in the art. Generally the flow rates will be within the range of about 0.10 to 10 liquid volumes of the organic compound to be dehydrogenated per volume of dehydrogenation zone containing catalyst per hour (referred to as LHSV). Usually, the LHSV will be between 0.15 and about 5. For calculation, the volume of a fixed bed dehydrogenation zone containing catalyst is that original void volume of reactor space containing catalyst.

The catalysts of this invention contain iron, oxygen and at least one other metallic element Me. The catalysts comprise crystalline compositions of iron, oxygen, and at least one other metallic element Me. The catalysts comprise ferrites. Ordinarily, the ionic radius of the second metallic ingredient(s) Me is small enough that the oxygen anions are not spread too far apart. That is, the elements must be able to form a crystalline structure with the iron and oxygen.

A preferred type of catalyst of this type is that having a face-centered cubic form of crystalline structure. Examples of this type of catalyst are ferrites of the general formula $MeO \cdot Fe_2O_3$ where Me is a divalent metal cation such as $Mg^{++}$ or $Ni^{++}$. However, if the cations are large, such as $Sr^{++}$ (1.35 A), the spinel structure may not occur and other types of ferrites having a hexagonal crystal of the type $SrO \cdot 6Fe_2O_3$ may be formed. These hexagonal ferrites are within the scope of the definition of catalysts of this invention.

Suitable catalysts may also be ferrites wherein other metals are partially substituted for the iron. For example, atoms having a valence of +3 may be partially substituted for some of the $Fe^{+++}$ atoms. Also, metal atoms having a valence of +4 may replace some of the $Fe^{+++}$ ions. However, the catalysts will still suitably have iron present in an amount described above in relation to the total atoms of the second metallic ingredient(s).

The catalysts may have the iron combined in crystalline structure with oxygen and more than one other metallic element, as mentioned above. For example, a preferred type of ferrite is that essentially or approximately of the formula, $MeFe_2O_4$, where Me represents a divalent metal ion with an ionic radius approximately between 0.5 and 1.1 A, preferably between about 0.6 and 1.0 A. In the case of simple ferrites, Me may be, e.g., one of the divalent ions of the transition elements as Mg, Ca, Sr, Ba, Cr, Mn, Co, Ni, Zn, or Cd. However, a combination of these ions is also possible to form a ferrite such as $Ni_{0.5}Mg_{0.5}Fe_2O_4$ or $Ni_{0.25}Mg_{0.75}Fe_2O_4$. Moreover, the symbol Me may represent a combination of ions which have an average valency of two. However, it is essential that the crystalline structure contain iron and the metallic element other than iron.

Examples of catalysts are such as magnesium ferrite, cobalt ferrite, nickel ferrite, zinc ferrite, barium ferrite, strontium ferrite, manganese ferrite, calcium ferrite, cadmium ferrite, silver ferrite, zirconium ferrite, and rare earth ferrites such as cerium ferrite or mixtures of ferrites, such as ferrites containing iron combined with at least one element selected from the group consisting of Mg, Zn, Ni, Co, Mn, Cu, Cd, Ca, Ba, Sr, Al, Cr, Ti, V, Mo, W, Na, Li, K, Sn, Pb, Sb, Bi, Ga, Ce, La, Th, other rare earth elements and mixtures thereof, with a preferred group being Mg, Ca, Sr, Ba, Mn, Cr, Co, Ni, Zn, Cd, and mixtures thereof, and particularly preferred metals being Mg or Mn. Examples of mixed ferrites are magnesium ferrite plus zinc ferrite, magnesium ferrite plus nickel ferrite magnesium ferrite plus cobalt ferrite, magnesium ferrite plus nickel ferrite plus zinc ferrite, magnesium ferrite plus manganese ferrite. As explained above, these ferrites may be physical mixtures of the ferrites or may contain crystals wherein the different metallic atoms are contained in the same crystal, or a combination of physical mixtures and chemical combinations. Some examples of a chemical combination would be magnesium zinc ferrite, magnesium chromium ferrite, zinc chromium ferrite and lanthanum chromium ferrite.

The valency of the metals in the catalysts do not have to be any particular values, although certain combinations are preferred or disclosed elsewhere. The determination of the valency of the ions is sometimes difficult and the results are uncertain. The different ions may exist in more than one valency state. However, a preferred catalyst is one which has the iron predominately in the $Fe^{+++}$ state. Some ferrites are described in Ferromagnetism, by Richard M. Bozorth (D. Van Nostrand Co., Inc., 1951), which disclosure is hereby incorporated by reference.

Although the catalysts may be broadly defined as containing crystalline structure of iron, oxygen and the second metallic ingredient(s), certain types of catalysts are preferred. Valuable catalysts were produced comprising as the main active constituent in the catalyst surface exposed to the reaction gases, iron, oxygen and at least one element selected from the group of Mn, or Periodic Table Groups IIA, IIB or VIII such as those selected from the group consisting of magnesium, manganese, calcium, cadmium, cobalt, zinc, nickel, barium, strontium, and mixtures thereof. The Periodic Table referred to is the one on pages 400–401 of the Handbook of Chemistry and Physics (39th edition, 1957–58, Chemical Rubber Publishing Co., Cleveland, Ohio). Preferred catalysts have iron present as the predominant metal in the catalyst exposed in the reaction gases.

A preferred class of catalysts containing two second metallic ingredients are those of the basic formula $Me_aCr_bFe_cO_4$ where $a$ can vary within the range of about 0.1 to about 3, $b$ can vary from greater than 0 to less than 2 and $c$ can vary from greater than 0 to less than 3. Me can be any of the metallic ingredients, other than chromium, previously described, particularly Periodic Table Groups IIA, IIB, III and VIII. In particularly, the metals from these groups that are desirable are Mg, Ba, La, Ni, Zn and Cd.

The preferred compositions exhibit a certain type of X-ray diffraction pattern. The preferred compositions do not have any sharp X-ray diffraction reflection peaks as would be found, e.g., in a highly crystalline material having the same chemical composition. Instead, the preferred compositions of this invention exhibit reflection peaks which are relatively broad. The degree of sharpness of the reflection peak may be measured by the reflection peak band width at half height (W h/2). In other words, the width of the reflection peak as measured at one-half of the distance to the top of the peak is the "band width at half height". The band width at half height is measured in units of °2 theta. Techniques for measuring the band widths are discussed, e.g., in Chapter 9 of Klug and Alexander, X-ray Diffraction Procedures, John Wiley and Son, N.Y., 1954. The observed band widths at half height of the preferred compositions of this invention are at least 0.16 °2 theta and normally will be at least 0.20 °2 theta.* For instance, excellent compositions have been made with band widths at half height of at least 0.22 or 0.23 °2 theta. The particular reflection peak used to measure the band width at one-half height is the reflection peak having Miller (hkl) indices of 220. (See, e.g., Chapter of Klug and Alexander, ibid). Applicants do not wish to be limited to any theory of the invention in regard to the relationship between composition activity and band width.

*The powder diffraction patterns may be made, e.g., with a Norelco constant potential diffraction unit type No. 12215/0 equipped with a wide range goniometer type No. 42273/0, cobalt tube type No. 32119, proportional counter type No. 57250/1; all coupled to the Norelco circuit panel type No. 12206/53. The cobalt K alpha radiation is supplied by operating the tube at a constant potential of 30 kilovolts and a current of 10 milliamperes. An iron filter is used to remove K beta radiation. The detector voltage is 1660 volts and the pulse height analyzer is set to accept pulses with amplitudes between 10 and 30 volts only. Slits used are divergence 1°, receiving 0.006 inches and scatter 1°. Strip chart recordings for identification are made with a scanning speed of ¼° per minute, time constant of 4 seconds and a full scale at $10^3$ counts per second. No correction is made for $K\alpha$ doublet or instrumental broadening of the band widths.

Suitable preferred ferrites according to this invention are zinc ferrites having X-ray diffraction peaks within the d-spacings 4.83 to 4.89, 2.95 to 3.01, 2.51 to 2.57, 2.40 to 2.46, 2.08 to 2.14, 1.69 to 1.75, 1.59 to 1.65 and 1.46 to 1.52, with the most intense peak being between 2.95 to 3.01; manganese ferrite having peaks at d spacings within or about 4.87 to 4.93, 2.97 to 3.03, 2.50 to 2.58, 2.09 to 2.15, 1.70 to 1.76, 1.61 to 1.67 and 1.47 to 1.53, (with other peaks) with the most intense peak being between 2.52 to 2.58; magnesium ferrites having peaks between 4.80 to 4.86, 2.93 to 2.99, 2.49 to 2.55, 2.06 to 2.12, 1.68 to 1.73, 1.58 to 1.63 and 1.45 to 1.50 with the most intense peak being between 2.49 and 2.55; and nickel ferrites having peaks within the d spacings of 4.79 to 4.85, 2.92 to 2.98, 2.48 to 2.54, 2.05 to 2.11, 1.57 to 1.63 and 1.44 to 1.49, with the most intense peak being within 2.48 to 2.54. The preferred manganese ferrites are those having the Mn predominately present as a valence of plus 2.

Ferrite formation may be accomplished by reacting an active compound of iron with an active compound of the designated metals. By active compound is meant a compound which is reactive under the conditions to form the ferrite. Starting compounds of iron or the other metal may be such as the nitrates, hydroxides, hydrates, oxalates, carbonates, acetates, formates, halides, oxides, etc. The starting compounds are suitably oxides or compounds which will decompose to oxides during the formation of the ferrite such as organic and inorganic salts or hydroxides. For example, manganese carbonate may be reacted with iron oxide hydrates to form manganese ferrite. Salts of the desired metals may be coprecipitated and the precipitate heated to form the ferrite. Desired ferrites may be obtained by conducting the reaction to form the ferrite at relatively low temperatures, that is, at temperatures lower than some of the very high temperatures used for the formation of some of the semi-conductor applications. Good results, e.g., have been obtained by heating the ingredients to a temperature high enough to produce the required ferrite but at conditions no more severe than equivalent to heating a 950° or 1000°C for 90 minutes in air and generally the maximum temperature will be less than 1300°C and preferably less than 1150°C. Methods for preparing catalysts suitable for this invention are disclosed in U.S. Pat. Nos. 3,270,080; 3,284,536; 3,303,234-6; 3,303,238; 3,308,182; 3,334,152; 3,342,890 and 3,450,787 and these disclosures are hereby incorporated by reference.

The solid sulfur containing compounds such as manganese sulfate can be incorporated along with manganese carbonate to form a sulfur containing manganese ferrite. Another method is to mix a ferrite, e.g. nickel ferrite with a solution of sulfuric acid. The resulting slurry can then be dried and pelleted or coated on a carrier and then dried.

The catalysts may contain an excess of iron over the stoichiometric amount to form the ferrite. For example, in a ferrite of the type $MeFe_2O_4$ the stoichiometric amount of iron would be 2 atoms per atom of Me. The iron (calculated as $Fe_2O_3$) may be present in an amount of at least about 10 percent in excess of the stoichiometric amount and preferably may be present in an amount of at least 14 percent in excess. Suitable ranges of iron are from about 10 to 200 percent excess. Similarly the catalysts may contain an excess of Me over the stoichiometric amount.

The compositions of this invention may also comprise additives, such as disclosed in U.S. Pat. Nos. 3,270,080 and 3,303,238. Phosphorus, silicon, boron or mixtures thereof are examples of additives. Excellent catalysts may contain less than 5 weight percent, and preferably less than 2 weight percent, of sodium or potassium in the surface of the catalyst.

Carriers or supports for the catalyst may be employed such as alumina, pumice, silica and so forth. Diluents and binders may also be used. Unless stated otherwise, the compositions referred to in this application are the main active constituents of the dehydrogenation process during dehydrogenation and any ratios and percentages refer to the surface of the catalyst in contact with the gaseous phase during dehydrogenation.

The catalysts may be activated or regenerated by reducing with a reducing gas, e.g., such as hydrogen or hydrocarbons. For example, the preformed compositions may be reduced with, e.g., hydrogen at a temperature or at least 250°C. with the temperature of reduction generally being no greater than 850°C. The period of time for reduction will be dependent somewhat on the temperature of reduction.

The process of this invention utilizes either a fixed bed or moving bed, such as a fluidized catalyst, reactor. Reactors which have been used for the dehydrogenation of hydrocarbons by non-oxidative dehydrogenation are satisfactory such as the reactors for the dehydrogenation of n-butene to butadiene-1,3. Although means to remove heat from the reactor may be employed, such as coils, the invention is particularly useful with essentially adiabatic reactors where heat removal is a problem.

The following examples are only illustrative of the invention and are not intended to limit the invention. All percentages are weight percent unless specified otherwise. All conversions, selectivities and yields are expressed in mol percent of the designated feed.

EXAMPLE 1

This example shows the improvement in a barium ferrite (Columbian Carbon Company barium ferrite type EG-4 deposited on low surface area alumina (AMC<1 m²/g). The sulfur promoter was incorporated in the catalyst during preparation. All runs were made in a Vycor glass reactor. The feed was butene-2 at a liquid hourly space velocity (LHSV) of 1. The feed to the reactor comprised butene-2/steam/oxygen in the ratio of 1/30/0.6. The temperature of the reaction was 525°C. The results are set out in Table I below:

TABLE I

| Run | Promoter | Conversion mole % | Selectivity mole% | Yield mole % Butadiene per pass |
|---|---|---|---|---|
| control | 0 | 20 | 25 | 5 |
| 1 | 6%(NH$_4$)$_2$SO$_4$ | 55 | 91 | 50 |
| 2 | 20%Al$_2$(SO$_4$)$_3$·18H$_2$O | 49 | 89 | 44 |
| 3 | 6%FeSO$_4$ | 51 | 89 | 45 |

% based on catalysts weight on support.

EXAMPLE 2

This example shows the improvement achieved by adding sulfur to a magnesium ferrite catalyst, prepared by depositing Fe(NO$_3$)$_3$ on MgO pellets, calcining at 900°C. and reducing with H$_2$ for 1 hour at 500°C. Magnesium sulfate (2.2 grams) was added to the Fe(NO$_3$)$_3$ solution (125 g Fe(NO$_3$)$_3$ · 9H$_2$O) to give 0.6 gram of sulfur, in 100 ml. H$_2$O which solution was then deposited on 50 grams of MgO pellets, calcined at 900°C., reduced with H$_2$ for 1 hour at 500°C. Similarly various other sulfur compounds as shown in Table II were added to the Fe(NO$_3$)$_3$ solution to give 0.6 grams of sulfur, calcined and reduced. Each run was made in a Vycor glass reactor with butene-2 at a flow of 1 LHSV. Steam was also present. The mole ratio of butene/steam/oxygen at a reaction temperature of 500°C. was 1/30/0.6. The results are shown in Table II.

TABLE II

| Run | Promoter | Conversion mole % | Selectivity mole% | Yield mole % Butadiene per pass |
|---|---|---|---|---|
| control | 0 | 40 | 87 | 35 |
| 1 | MgSO$_4$ | 75 | 92 | 69 |
| 2 | Cr$_2$(SO$_4$)$_3$ | 72 | 93 | 67 |
| 3 | NH$_4$SCN | 57 | 94 | 53 |
| 4 | (NH$_4$)$_2$S$_2$O$_8$ | 57 | 95 | 54 |

EXAMPLE 3

A nickel ferrite was prepared by mixing nickel oxide and ferric oxide in the presence of water. The slurry was dewatered and dried. The dried mixture was then calcined at 900°C. for 1–1½ hours. Promoted catalysts were prepared by adding 10% FeSO$_4$ and 10% NiSO$_4$ to separate portions of the catalyst prior to calcining. Butene-2, oxygen and steam were fed at a mole ratio of 1/0.6/30. The LHSV of butene-2 was 1.0. The temperatures of reactions and results are shown in Table III.

TABLE III

| Run | Temp. | Promoter | Conversion mole % | Selectivity mole % | Yield mole % Butadiene per pass |
|---|---|---|---|---|---|
| control | 430 | 0 | 59 | 92 | 54 |
| 1 | 420 | 10%FeSO$_4$ | 65 | 90 | 58 |
| 2 | 420 | 10%NiSO$_4$ | 66 | 92 | 61 |

EXAMPLE 4

50 grams MgO pellets (38% porosity) were impregnated under vacuum with iron nitrate solutions (125g Fe(NO$_3$)$_3$ · 9H$_2$O in 150 ml. of water) the impregnated pellets and excess ferric nitrate was transferred to a porcelain dish and decomposed over an open flame. One portion of the coated pellets were calcined for 1 hour at 900°C. Another portion of the catalyst was reduced with H$_2$ for 1 hour at 500°C. A portion of both catalysts was further treated with 1 cc. of concentrated (approx. 96%) H$_2$SO$_4$. The conversion of butene-2 to butadiene was significantly improved by the addition of H$_2$SO$_4$. The results are shown in Table IV below:

TABLE IV[1]

| Run | Catalyst Preparation | Promoter | Temps. of Reaction °C. | C | S | Y |
|---|---|---|---|---|---|---|
| control | calc. 1 hr. at 900°C. | 0 | 575 | 38 | 76 | 29 |
| 1 | calc. 1 hr. at 900°C. | 1 cc. conc. | 550 | 32 | 95 | 30 |
| control | red. w/H$_2$— 1 hr. at 500°C | 0 | 450 | 30 | 89 | 27 |
| 2 | red. w/H$_2$—1 hr at 500°C. | H$_2$SO$_4$ | 475 | 55 | 95 | 52 |
| | | | | mole % | mole % | mole % butadiene per pass |

[1] Butene-2 feed at LHSV of 1.0 at a mole ratio of butene-2/O$_2$/steam of 1/0.6/30

[2] Conversion/selectivity/yield

EXAMPLE 5

A catalyst was prepared according to Example 4 but with $MgSO_4$ (2.2g) added to iron nitrate solution at 500°C. Under the same conditions and reactants as Example 4 the catalyst reduced for 1 hour with $H_2$ at 500°C. gave C/S/Y of 62/94/58.

EXAMPLE 6

In a manner similar to Example 5 various sulfur compounds were added to the iron nitrate solution. The sulfur content was maintained at about 0.5 wt % of the catalyst. The same reactants and conditions as in Example 4 and 5 were employed. At 500°C. the results shown in Table V were obtained.

TABLE V

| Run | Cat. preparation | Promoter | C | S | Y |
|---|---|---|---|---|---|
| control | calc. at 900°C. for 1 hour | 0 | 16 | 88 | 14* |
|  | " |  | 38 | 76 | 29** |
| 1 | " | $CdSO_4$ | 49 | 95 | 47 |
| 2 | " | $MnSO_4$ | 37 | 97 | 36 |
| 3 | " | $MgSO_4$ | 44 | 98 | 43 |
| 4 | " | $(NH_4)_2SO_4$ | 29 | 97 | 28 |
| 5 | " | $ZnSO_4$ | 47 | 98 | 46 |
| 6 | " | $NiSO_4$ | 40 | 97 | 39 |
| 7 | " | $NH_4SCN$ | 42 | 91 | 38 |
| control | calc. at 900°C. for 1 hr. and red. w/$H_2$ for 1 hr. at 550°C | 0 | 40 | 87 | 35 |
| 8 | " | $FeSO_4$ | 43 | 88 | 38 |
| 9 | " | $CdSO_4$ | 46 | 91 | 42 |
| 10 | " | $ZnSO_4$ | 57 | 92 | 52 |
| 11 | " | $NiSO_4$ | 60 | 93 | 56 |
| 12 | " | $NH_4SCN$ | 57 | 94 | 53 |

*475°C.
**575°C.

EXAMPLE 7

A nickel ferrite prepared according to Example 3 exhibits some improvement when treated prior to use with gaseous $SO_2$. The C/S/Y of butene-2 (LHSV-1, butene-2/oxygen/steam mol ratio of 1/0.6/30) over untreated catalyst is 59/92/54 (430°C.) over the treated catalyst 66/90/59 (430°C.)

EXAMPLE 8

The oxidative dehydrogenation yield of a manganese ferrite prepared by calcining ferric oxide and manganous carbonate at 800°C. for 1 hour was increased and stabilized by the incremental addition $H_2SO_4$ as shown in Table VI.

TABLE VI

| Run | Promoter | Reaction Temp.[1] °C. | C | S | Y[2] |
|---|---|---|---|---|---|
| control | 0 | 400 | 47 | 84 | 40 |
| " |  | 490 | 25 | 55 | 14 |
| 1 | .13g $H_2SO_4$[3] | 485 | 57 | 87 | 50 |
| 2 | .39g $H_2SO_4$[3] | 450 | 68 | 91 | 62 |
| 3 | 0 | 455 | 66 | 90 | 60 |

[1]butene-2 LHSV = 1 Bu-2/$O_2$/$H_2O$ 1/0.6/30
[2]Conversion/selectivity/yield mole % butadiene
[3]Concentrated 96% added with the feed.

Run 3 demonstrates the stabilizing effect of the $H_2SO_4$ previously added with the feed to Runs 1 and 2.

EXAMPLE 9

This example shows the activation of some metal ferrite catalyst by the addition of $H_2SO_4$ with the butene-2 feed. The catalysts were prepared by calcining a mixture of ferric oxide and the metal carbonate at 900°C. for 1 hour. The results are shown in Table VII.

TABLE VII

| Run | Catalyst | Promoter | Conversion/selectivity/yield, mole percent butadiene Temperature of Reaction[1] | | | | |
|---|---|---|---|---|---|---|---|
|  |  |  | 450°C. | 500°C. | 525°C. | 550°C. | 600°C. |
| 1 | Barium ferrite | 0 | 10/27/3 | 11/24/3 | — | — | — |
| 2 | " | 0.4 ml. conc. $H_2SO_4$/hr in feed | 52/91/47 | 50/90/45[2] | — | — | — |
| 3 | Strontium ferrite | 0 | — | 8/35/3 | — | 12/32/4 | 15/30/5 |
| 4 | " | L cc. conc. $H_2SO_4$/hr in feed | — | 58/90/52 | — | 58/87/50 | 46/85/39 |
| 5 | Calcium ferrite | 0 | — | — | 14/33/5 | — | — |
| 6 | " | 2. cc conc. $H_2SO_4$/hr in feed | — | — | 37/83/31 | — | — |
| 7 | Cobalt ferrite | 0 | 9/85/7 | 18/79/14 | — | 24/71/17 | 31/59/18 |
| 8 | " | 2. cc conc. $H_2SO_4$/hr in feed | — | — | — | 10/96/10 | 29/92/27 |

[1]Feed Butene-2 at 1 LHSV, mole ratio Bu-2/$O_2$/$H_2O$ = 1/0.6.30
[2]475°C.

EXAMPLE 10

This example shows the activation of rare earth and other less common metal ferrites by addition of a sulfur compound prior to calcining. The metal ferrite was prepared by calcining the mixed metal compounds shown in Table VIII at 900°C. for 1 hour.

TABLE VIII

| Run | Catalyst | Promoter | Temp. of Reaction °C | (1)Conv./Selec./Yield mole % butadiene |
|---|---|---|---|---|
| 1 | $Fe_2O_3.H_2O.HCl_4$ | 0 | 540 | 27/46/12 |
| 2 | " | 0.26g $H_2SO_4$ (96%) | 540 | 30/59/17 |
| 3 | $Fe_2O_3$—$SrCO_3$(2) | 0 | 500 | 13/16/2 |
| 4 | " | 1.04g $H_2SO_4$ (96%) | 440 | 56/89/50 |
| 5 | $Fe_2O_3$—$CeO_2.H2O$ | 0 | 600 | 25/42/11 |
| 6 | " | 0.63g$H_2SO_4$ (96%) | 510 | 34/77/26 |
| 7(4) | $Fe_2O_3$—$Di_2O_3$(3) 0.5 wt% $DiCl_3$ | 0 | 450 | 34/73/25 |
| 8(4) | " | 0.26g $H_2SO_4$ (96%) | 460 | 39/83/32 |

(1)Butene-2/$O_2$/$H_2O$ = 1/0.6/30 LHSV=1
(2)Calcined at 950°C.
(3)Di=didymium is used here to describe a mixture of rare earths, e.g. a $Di_2O_3$ is typically 45–46% $La_2O_3$, 1–2% $CeO_2$, 9–10% $Pr_6O_{11}$, 32–33% $Nd_2O_3$, 5–6% $Sm_2O_3$, 3–4% $Gd_2O_3$, 0.4% $Yb_2O_3$ and 1–2% other rare earths
(4)Bu-2/$O_2$/He = 1/0.6/20 LHSV = 1

EXAMPLE 11

This example shows the improved results of a magnesium ferrite on a catalyst support. The conditions and results are reported in Table IX.

TABLE IX

| CATALYST | LHSV | (1)Conversion/Selectivity/Yield, mole % to Butadiene Temp., °C. | | | | |
|---|---|---|---|---|---|---|
| | | 450 | 475 | 500 | 525 | 550 |
| $Fe_2O_3$+MgO on 100S(2) | 1 | — | — | 14/47/6 | 13/45/6 | — |
| $Fe_2O_3$+MgO on 100S(2)+.4 cc $H_2SO_4$ (96%)/hr in feed | 1 | — | — | — | 36/88/32 | 37/87/32 |

(1)Bu-2/$O_2$/Steam 1/0.6/30 LHSV = 1
(2)Coated pellets calcined 4 hrs. at 1100°C. Houdry 100S 98.5% alumina, 0.1–0.2 $Na_2O$

EXAMPLE 12

This example was carried out in a fixed bed small scale adiabatic unit having a stainless steel reactor. The catalyst was magnesium ferrite treated with phosphoric acid to have a 3% phosphorus content. The feed was butene-2. The promoter, reactor conditions and results are set forth in Table X.

TABLE X

| Run No. | ADDITION OF SULFUR | | | | REACTOR CONDITIONS | | | | | RESULTS | | |
|---|---|---|---|---|---|---|---|---|---|---|---|---|
| | Hrs(1) | Promoter | conc.(2) (ppm) | Gms.(3) | LHSV | mole ratio steam/HC | $O_2$/$C_4$(4) | Tin(5) °F. | Tmax(6) °F. | C | S | Y |
| 1 | | | 0 | | 2.24 | 13.2 | 0.60 | 749 | 1140 | 58.4 | 90.6 | 53 |
| | 12 | $CH_3SH$ | 30 | 12.3 | 2.24 | 13.2 | 0.60 | 747 | 1124 | 62.8 | 92.1 | 57.8 |
| 2 | | | 0 | | 2.24 | 13.2 | 0.60 | 747 | 1140 | 59.4 | 90.6 | 53.8 |
| | 23 | $CH_3SH$ | 50 | 38.1 | 2.24 | 13.2 | 0.60 | 745 | 1117 | 61.4 | 92.3 | 56.7 |
| 3 | | | 0 | | 2.27 | 13.0 | 0.50 | 740 | 1105 | 54.9 | 92.5 | 50.8 |
| | 85 | $CH_3SH$ | 30 | 87.0 | 2.27 | 13.0 | 0.50 | 740 | 1095 | 59.3 | 93.5 | 55.5 |
| 4 | | | 0 | | 2.27 | 13.2 | 0.51 | 740 | 1097 | 57.3 | 93.0 | 53.3 |
| | 30 | $SO_2$ | 15 | 57 | 2.27 | 13.2 | 0.51 | 740 | 1076 | 60.3 | 93.7 | 56.5 |
| 5 | | | 0 | | 2.27 | 13.2 | 0.51 | 740 | 1090 | 57.6 | 92.8 | 53.5 |
| | 50 | $SO_2$ | 5 | 8.6 | 2.27 | 13.2 | 0.51 | 740 | 1088 | 60.6 | 93.4 | 56.6 |
| 6 | | | 0 | | 2.27 | 14.8 | 0.73 | 710 | 1160 | 67.2 | 89.6 | 60.2 |
| | 13 | $SO_2$ | 7 | 3.2 | 2.27 | 14.8 | 0.73 | 710 | 1145 | 69.8 | 90.5 | 63.2 |
| 7 | | | 0 | | 2.26 | 14.8 | 0.73 | 710 | 1150 | 66.5 | 88.8 | 59.1 |
| | 49 | $CS_2$ | 14 | 23.2 | 2.26 | 14.4 | 0.73 | 710 | 1135 | 69.2 | 90.7 | 62.8 |
| 8 | | | 0 | | 2.26 | 14.4 | 0.73 | 710 | 1160 | 66.9 | 90.1 | 60.2 |
| | 44 | $CH_3SH$ | 20 | 30.0 | 2.26 | 14.4 | 0.73 | 710 | 1150 | 68.4 | 90.9 | 62.2 |
| 9 | | | 0 | | 2.26 | 14.4 | 0.73 | 710 | 1160 | 66.7 | 90.0 | 60.0 |
| | 13 | $CH_3SH$ | 4 | 2.4 | 2.26 | 14.4 | 0.73 | 710 | 1150 | 67.5 | 90.2 | 60.8 |
| 10 | | | 0 | | 2.26 | 14.4 | 0.71 | 710 | 1140 | 64.2 | 89.3 | 57.3 |
| | 41 | $CH_3SH$ | 3 | 4.2 | 2.26 | 14.4 | 0.71 | 710 | 1130 | 63.9 | 89.9 | 57.4 |
| | 53 | | 6 | 10.8 | 2.26 | 14.4 | 0.71 | 710 | 1128 | 67.4 | 90.9 | 61.3 |

(1)Total hours that sulfur compound was fed to the reactor.
(2)Concentration ppm based on hydrocarbon feed.
(3)Total grains of sulfur feed.
(4)$C_4$ = butene-2
(5)Tin = inlet temperature °F.
(6)Tmax. = maximum temperature in bed °F.

We claim:
1. A process for the oxidative dehydrogenation of organic compounds in the presence of an oxygen containing gas, a metal ferrite catalyst, and at least a promoting amount of sulfur.
2. The process according to claim 1 wherein the metal has an ionic radius approximately between 0.5 and 1.1 A.
3. The process according to claim 1 wherein the metal is selected from the group consisting of Mg, Zn,

Ni, Co, Mn, Cu, Cd, Ca, Ba, Sr, Al, Cr, Ti, V, Mo, W, Na, Li, K, Sn, Pb, Sb, Bi, Ga, Ce, La, the other rare earths and mixtures thereof.

4. The process according to claim 3 wherein the metal is selected from the group consisting of Mg, Ca, Sr, Ba, Mn, Cr, Co, Ni, Zn, Cd, and mixtures thereof.

5. The process according to claim 4 wherein the metal is Mg or Mn.

6. The process according to claim 4 wherein the metal is comprised of at least two components.

7. The process according to claim 6 wherein one of the components is Cr.

8. The process according to claim 7 wherein the second metal component is a metal selected from Periodic Table Groups IIA, IIB, III, and VII.

9. The process according to claim 1 wherein said organic compounds are hydrocarbons.

10. The process according to claim 9 wherein butene is oxidatively dehydrogenated.

11. The process for the oxidative dehydrogenation of organic compounds according to claim 1 wherein the sulfur is incorporated in the metal ferrite catalyst in a ratio of 0.001 to 0.5 atom of sulfur per atom of iron in said catalyst prior to the contact of said catalyst with the organic compounds.

12. The process according to claim 11 wherein the metal has an ionic radius approximately between 0.5 and 1.1 A.

13. The process according to claim 11 wherein the metal is selected from the group consisting of Mg, Zn, Ni, Co, Mn, Cu, Cd, Ca, Ba, Sr, Al, Cr, Ti, V, Mo, W, Na, Li, K, Sn, Pb, Sb, Bi, Ga, Ce, La, the other rare earths and mixtures thereof.

14. The process according to claim 13 wherein the metal is selected from the group consisting of Mg, Ca, Sr, Ba, Mn, Cr, Co, Ni, Zn, Cd, and mixtures thereof.

15. The process according to claim 14 wherein the metal is Mg or Mn.

16. The process according to claim 11 wherein the metal is comprised of at least two components.

17. The process according to claim 16 wherein one of the components is Cr.

18. The process according to claim 17 wherein the second metal component is a metal selected from Periodic Table Groups IIA, IIB, III, and VIII.

19. The process according to claim 11 wherein said organic compounds are hydrocarbons.

20. The process according to claim 19 wherein butene is oxidatively dehydrogenated.

21. The process for the oxidative dehydrogenation of organic compounds according to claim 1 wherein sulfur is added to the reaction in a mole ratio of sulfur to organic compounds of between 0.0003:1 and 0.5:1.

22. The process according to claim 21 wherein there is a ratio of gram atoms of sulfur to a mole organic compounds of between about 0.001 : 1.0 to 0.05 : 1.0.

23. The process according to claim 21 wherein the metal has an ionic radius approximately between 0.5 and 1.1 A.

24. The process according to claim 21 wherein the metal is selected from the group consisting of Mg, Zn, Ni, Co, Mn, Cu, Cd, Ca, Ba, Sr, Al, Cr, Ti, V, Mo, W, Na, Li, K, Sn, Pb, Sb, Bi, Ga, Ce, La, the oher rare earths and mixtures thereof.

25. The process according to claim 24 wherein the metal is selected from the group consisting of Mg, Ca, Sr, Ba, Mn, Cr, Co, Ni, Zn, Cd, and mixtures thereof.

26. The process according to claim 25 wherein the metal is Mg or Mn.

27. The process according to claim 21 wherein the metal is comprised of at least two components.

28. The process according to claim 27 wherein one of the components is Cr.

29. The process according to claim 28 wherein the second metal component is a metal selected from Periodic Table Groups IIA, IIB, III, and VIII.

30. The process according to claim 21 wherein said organic compounds are hydrocarbons.

31. The process according to claim 30 wherein butene is oxidatively dehydrogenated.

32. A process for the dehydrogenation of ethylbenzene to styrene comprising:
contacting ethylbenzene and $SO_2$ in the vapor phase under dehydrogenation conditions with a catalyst comprising:
a ferrite of the spinel form having the formula
$A_a A'_b Fe_c O_4$ 
where A has a valence of plus 2 and is a metal selected from the group consisting of cobalt, nickel, zinc and magnesium; A' has a valence of plus 3 and is selected from the group consisting of chromium and lanthanum; $a$ has a value from 0.1 to about 3; $b$ has a value from 0 to less than 2; $c$ has a value from greater than 0 to about 3; and $a+b+c$ has a value of 3; or a ferrite of the perovskite form having the formula
$B_d Cr_e Fe_f O_3$ 
where B has a valence of plus 3 and is selected from lanthanum and yttrium; $d$, $e$ and $f$ are each values from 0.5 to 1.5 and the sum of $d$, $e$, and $f$ is 2.

33. A process according to claim 32 wherein the catalyst is a ferrite of the perovskite form having the formula
$B_d Cr_e Fe_f O_3$ 
where B has a valence of plus 3 and is selected from lanthanum and yttrium; $d$, $e$ and $f$ are each values from 0.5 to 1.5 and the sum of $d$, $e$ and $f$ is 2.

34. A process according to claim 33 wherein B is lanthanum.

35. A process according to claim 32 wherein the catalyst is a ferrite of the spinel form having the formula
$A_a A'_b Fe_c O_4$ 
where A is a metal selected from the group consisting of cobalt, nickel, zinc and magnesium; A' is a metal selected from chromium and lanthanum; $a$ has a value from 0.1 to about 3; $b$ has a value from 0 to less than 2; $c$ has a value from greater than 0 to about 3; and $a+b+c$ has a value of 3.

36. A process according to claim 35 wherein the catalyst has the formula
$A A'_x Fe_y O_4$ 
where A has a valence of plus 2 and is a metal selected from the group consisting of cobalt, nickel, zinc, and magnesium; A' is a metal having a valence of plus 3 and is selected from the group consisting of chromium and lanthanum; and $x$ is a value from 0 to 1.5; $y$ is a value from 0.5 to 2 and $x$ plus $y$ has a value equal to 2.

37. A process according to claim 36 wherein A is selected from zinc and magnesium; A' is chromium; $x$ has a value from 0 to 1, $y$ has a value from 1 to 2, and the sum of the values of $x$ and $y$ is 2.

38. A process according to claim 37 wherein the catalyst is $ZnCrFeO_4$.

39. A process according to claim 37 wherein the catalyst is $MgCrFeO_4$.

40. A process according to claim 35 wherein the dehydrogenation conditions include a temperature from 300° to 700°C.

41. A process according to claim 32 wherein a diluent gas is also present.

42. A cyclic process for the dehydrogenation of ethylbenzene to produce styrene which comprises:
1. contacting ethylbenzene with $SO_2$ in the vapor phase under dehydrogenation conditions with a catalyst comprising:
a ferrite of the spinel form having the formula
$$A_a A'_b Fe_c O_4$$
where A has a valence of plus 2 and is a metal selected from the group consisting of cobalt, nickel, zinc and magnesium; A' is a metal having a valence of plus 3 and is selected from the group consisting of chromium and lanthanum; $a$ has a value from 0.1 to about 3; $b$ has a value from 0 to less than 2; $c$ has a value from greater than 0 to about 3; and $a+b+c$ has a value of 3; or a ferrite of the perovskite form having the formula
$$B_d Cr_e Fe_f O_3$$
where B has a valence of plus 3 and is selected from lanthanum and yttrium; $d$, $e$ and $f$ are each values from 0.5 to 1.5 and the sum of $d$, $e$ and $f$ is 2;
2. regenerating said ferrite catalyst with a gas containing free molecular oxygen;
3. contacting ethylbenzene and $SO_2$ in the vapor phase under dehydrogenation conditions with said regenerated ferrite catalyst to obtain substantially the same yields of styrene as were obtained initially.

43. A proces according to claim 42 wherein the dehydrogenation conditions include a temperature from 300° to 700°C, a liquid hourly space velocity of ethylbenzene from 0.15 to about 5.

44. A process according to claim 43 wherein the surface area of the catalyst is less than 10 m.²/gram.

45. A process according to claim 44 wherein a diluent gas is also present.

46. A process for the dehydrogenation of ethylbenzene to styrene comprising:
contacting ethylbenzene and $SO_2$ in the vapor phase under dehydrogenation conditions with a catalyst comprising:
a ferrite having two elements other than iron and oxygen with said elements being selected from the group consisting of (1) (a) a member selected from the group consisting of cobalt, nickel, zinc and magnesium together with (b) a metal selected from the group consisting of chromium and lanthanum or (2) a member selected from the group consisting of (a) lanthanum and yttrium together with (b) chromium.

47. A process according to claim 46 wherein (1) (b) is chromium and (2) (a) is lanthanum.

48. A process according to claim 41 wherein the molar ratio of diluent to ethylbenzene is from 3 to 35; the $SO_2$ to ethylbenzene ratio is from 0.0003 : 1.0 to 0.50 : 1.0 calculated as gram atoms of sulfur; and the liquid hourly space velocity of the ethylbenzene is from 0.1 to 10.

49. A process according to claim 46 wherein the said $SO_2$ is fed incrementally to said process.

50. A process for the dehydrogenation of ethylbenzene to styrene comprising:
contacting ethylbenzene and $SO_2$ in the vapor phase under dehydrogenation conditions with a catalyst comprising:
a ferrite selected from the group consisting of magnesium chromium ferrite, zinc chromium ferrite, lanthanum chromiun ferrite, nickel chromium ferrite and cobalt chromium ferrite.

51. The process of claim 50 wherein the catalyst comprises lanthanum chromium ferrite.

52. The process of claim 50 wherein the catalyst comprises nickel chromium ferrite.

* * * * *

UNITED STATES PATENT OFFICE
CERTIFICATE OF CORRECTION

PATENT NO. : 3,937,746
DATED : February 10, 1976
INVENTOR(S) : Louis J. Croce and Laimonis Bajars It is certified that error appears in the above-identified patent and that said Letters Patent are hereby corrected as shown below:

Line 2, IN THE ABSTRACT, reads "by having a surfur promoter", but should read ---- by having a sulfur promoter ----.

Col. 2, lines 45-49 reads "
$$\begin{array}{c} H \phantom{x} H \\ | \phantom{x} | \\ -C-C- \end{array}$$
", but should read ----
$$\begin{array}{c} H \phantom{x} H \\ | \phantom{x} | \\ -C-C- \\ | \phantom{x} | \end{array}$$
----

Col. 3, line 12, reads "alkphatic", but should read ---- aliphatic ----.
Col. 3, line 25, reads "non-quarternary", but should read ---- non-quaternary ----.
Col. 3, line 29, reads "quarternary", but should read ---- quaternary ----.
Col. 3, line 32, reads "quarternary", but should read ---- quaternary ----.
Col. 3, line 44, reads "non-quarternary", but should read ---- non-quaternary ----.
Col. 4, line 50, reads "incuding", but should read ---- including ----.
Col. 6, lines 22 and 23, reads "predominately", but should read ---- predominantly ----.
Col. 7, line 41, reads "predominately", but should read ---- predominantly ----.
Col. 7, line 65, reads "a 950°C", but should read ---- at 950°C ----.

UNITED STATES PATENT OFFICE
CERTIFICATE OF CORRECTION

PATENT NO. : 3,937,746
DATED : February 10, 1976
INVENTOR(S) : Louis J. Croce and Laimonis Bajars It is certified that error appears in the above-identified patent and that said Letters Patent are hereby corrected as shown below:

Col. 10, Table IV reads,"

TABLE IV[1]

| Run | Catalyst Preparation | Promoter | Temps. of Reaction °C | C | S | Y |
|---|---|---|---|---|---|---|
| control | calc. 1 hr. at 900°C. | 0 | 575 | 38 | 76 | 29 |
| 1 | calc. 1 hr. at 900°C. | 1 cc. conc. | 550 | 32 | 95 | 30 |
| control | red. w/H$_2$ — 1 hr. at 500°C | 0 | 450 | 30 | 89 | 27 |
| 2 | red. w/H$_2$ — 1 hr at 500°C. | H$_2$SO$_4$ | 475 | 55 | 95 | 52 |
| | | mole % | | mole % | mole % | mole % butadiene per pass |

[1]Butene-2 feed at LHSV of 1.0 at a mole ratio of butene-2/O$_2$/steam of 1/0.6/30

[2]Conversion/selectivity/yield but should read ----

TABLE IV.[1]

| Run | Catalyst Preparation | Promoter | Temps. of Reaction °C. | C[2] | S[2] | Y[2] |
|---|---|---|---|---|---|---|
| control | calc. 1 hr. at 900°C. | 0 | 575 | 38 | 76 | 29 |
| 1 | calc. 1 hr. at 900°C. | 1 cc. conc. | 550 | 32 | 95 | 30 |
| control | red. w/H$_2$ - 1 hr. at 500°C | 0 | 450 | 30 | 89 | 27 |
| 2 | red. w/H$_2$-1 hr at 500°C. | H$_2$SO$_4$ | 475 | 55 | 95 | 52 |

[1]Butene-2 feed at LHSV of 1.0 at a mole ratio of butene-2/O$_2$/steam of 1/0.6/30

[2]Conversion/selectivity/yield
mole %    mole %    mole % butadiene per pass

UNITED STATES PATENT OFFICE
CERTIFICATE OF CORRECTION

PATENT NO. : 3,937,746
DATED : February 10, 1976
INVENTOR(S) : Louis J. Croce and Laimonis Bajars It is certified that error appears in the above-identified patent and that said Letters Patent are hereby corrected as shown below:

Col. 11 and 12, Table VII, under "Promoter" column, reads "L cc. conc. $H_2WO_4$/hr." but should read---- 1. cc. conc. $H_2SO_4$/hr. ----.

Col. 13, Table VIII, under "Catalyst" column, reads "$Fe_2O_3 \cdot H_2O \cdot HCl_4$", but should read----$Fe_2O_3 \cdot H_2O-TiCl_4$----.

Col. 13, Table VIII, under "Promoter" column, reads "$0.63gH_2SO_4$", but should read----$0.65gH_2SO_4$----.

Col. 13, Table VIII, under "Catalyst" column, reads "5 $Fe_2O_3-CeO_2 \cdot H2O$" but should read----5 $Fe_2O_3-CeO_2 \cdot H_2O$----.

Col. 13 and 14, Table X, Footnote (3), reads "Total grains of sulfur feed.", but should read----Total grams of sulfur feed.... .

Col. 15, line 15, Claim 8, reads " Table Groups IIA, IIB, III, and VII", but should read----Table Groups IIA, IIB, III, and VIII----

Col. 15, line 63, Claim 24, reads "The oher rare earths", but should read----The other rare earths----, per Amendment R.111, filed December 13, 1972.

Col. 17, line 33, Claim 43, reads "A proces", but should read---- A process----, per Amendment R.111, filed December 13, 1972.

Signed and Sealed this

Sixteenth Day of November 1976

[SEAL]

Attest:

RUTH C. MASON
Attesting Officer

C. MARSHALL DANN
Commissioner of Patents and Trademarks